(12) United States Patent
Austen

(10) Patent No.: US 11,337,720 B2
(45) Date of Patent: May 24, 2022

(54) METHOD AND APPARATUS FOR DAMAGE AND REMOVAL OF FAT

(71) Applicant: The General Hospital Corporation, Boston, MA (US)

(72) Inventor: William G. Austen, Weston, MA (US)

(73) Assignee: The General Hospital Corporation, Boston, MA (US)

( * ) Notice: Subject to any disclaimer, the term of this patent is extended or adjusted under 35 U.S.C. 154(b) by 487 days.

(21) Appl. No.: 15/916,020

(22) Filed: Mar. 8, 2018

(65) Prior Publication Data

US 2018/0193054 A1 Jul. 12, 2018

Related U.S. Application Data

(62) Division of application No. 14/233,985, filed as application No. PCT/US2014/047708 on Jul. 20, 2012, now abandoned.

(Continued)

(51) Int. Cl.
*A61B 17/3205* (2006.01)
*A61B 17/20* (2006.01)
(Continued)

(52) U.S. Cl.
CPC ...... *A61B 17/32053* (2013.01); *A61B 17/205* (2013.01); *A61M 1/84* (2021.05);
(Continued)

(58) Field of Classification Search
CPC ............ A61B 10/0266; A61B 10/0275; A61B 10/0283; A61B 2017/320064;
(Continued)

(56) References Cited

U.S. PATENT DOCUMENTS 3,001,522 A 9/1961 Silverman
3,683,892 A 8/1972 Harris
(Continued)

FOREIGN PATENT DOCUMENTS

CA 2361777 A1 5/2002
CN 201005966 Y 1/2008
(Continued)

OTHER PUBLICATIONS

Bedi, et al., The Effects of Pulse Energy Variations on the Dimensions of Microscopic Thermal Treatment Zones in Nonablative Fractional Resurfacing, Lasers in Surgery and Medicine, 2007, 39:145-155.
(Continued)

*Primary Examiner* — Adam Marcetich
(74) *Attorney, Agent, or Firm* — Quarles & Brady LLP

(57) ABSTRACT

Exemplary embodiments of method and apparatus are provided for damaging and/or removing portions of subcutaneous fatty tissue while leaving the overlying dermal layer of the skin substantially undamaged. One or more hollow needles can be provided that include an arrangement within the lumen configured to retain or damage portions of fatty tissue that enter the lumen. Properties of the needle can be selected such that the needle can be inserted into skin and pass through the dermal layer, allowing fatty tissue to enter the distal portion of the lumen as it is advanced further, and then leaving the dermis undamaged when withdrawn. Such exemplary apparatus can include a plurality of such needles, a reciprocating arrangement to mechanically advance and withdraw the one or more needles, and/or a vibrating arrangement.

18 Claims, 4 Drawing Sheets

Related U.S. Application Data

(60) Provisional application No. 61/510,242, filed on Jul. 21, 2011.

(51) Int. Cl.
  *A61M 5/158* (2006.01)
  *A61M 1/00* (2006.01)
  *A61B 17/32* (2006.01)
  *A61B 17/00* (2006.01)

(52) U.S. Cl.
  CPC ... *A61M 5/158* (2013.01); *A61B 2017/00792* (2013.01); *A61B 2017/32004* (2013.01); *A61B 2017/320064* (2013.01); *A61M 2202/08* (2013.01)

(58) Field of Classification Search
  CPC .... A61B 17/32053; A61B 2017/00752; A61B 2010/0225; A61B 2018/00458; A61B 2018/00464; A61M 2202/09; A61M 2202/092; A61M 2202/097; A61M 5/3295; A61M 5/3297; A61M 5/3298; A61M 37/0015
  See application file for complete search history.

(56) References Cited

U.S. PATENT DOCUMENTS

| | | | |
|---|---|---|---|
| 3,867,942 A * | 2/1975 | Bellantoni | A61B 17/32053 |
| | | | 606/131 |
| 3,929,123 A | 12/1975 | Jamshidi | |
| 4,108,096 A | 8/1978 | Ciecior | |
| 4,167,179 A * | 9/1979 | Kirsch | A61N 5/1027 |
| | | | 600/7 |
| 4,476,864 A * | 10/1984 | Tezel | A61B 17/32053 |
| | | | 600/567 |
| 4,649,918 A | 3/1987 | Pegg et al. | |
| 4,865,026 A | 9/1989 | Barrett | |
| 4,903,709 A | 2/1990 | Skinner | |
| 5,269,316 A | 12/1993 | Spitalny | |
| 5,415,182 A * | 5/1995 | Chin | A61B 10/0275 |
| | | | 600/562 |
| 5,417,683 A * | 5/1995 | Shiao | A61B 17/3468 |
| | | | 604/173 |
| 5,458,112 A | 10/1995 | Weaver | |
| 5,615,690 A | 4/1997 | Giurtino et al. | |
| 5,643,308 A * | 7/1997 | Markman | A61B 17/3468 |
| | | | 606/1 |
| 5,749,895 A | 5/1998 | Sawyer et al. | |
| 5,885,211 A | 3/1999 | Eppstein et al. | |
| 5,922,000 A | 7/1999 | Chodorow | |
| 6,022,324 A | 2/2000 | Skinner | |
| 6,211,598 B1 | 4/2001 | Dhuler et al. | |
| 6,241,687 B1 | 6/2001 | Voegele et al. | |
| 6,251,097 B1 | 6/2001 | Kline et al. | |
| 6,264,618 B1 | 7/2001 | Landi et al. | |
| 6,432,098 B1 | 8/2002 | Kline et al. | |
| 6,461,369 B1 | 10/2002 | Kim | |
| 6,494,844 B1 * | 12/2002 | Van Bladel | A61B 18/02 |
| | | | 600/567 |
| 6,562,037 B2 | 5/2003 | Paton et al. | |
| 6,669,618 B2 | 12/2003 | Reising et al. | |
| 6,669,694 B2 | 12/2003 | Shadduck | |
| 6,733,496 B2 | 5/2004 | Sharkey et al. | |
| 6,893,388 B2 | 5/2005 | Reising et al. | |
| 6,936,039 B2 | 8/2005 | Kline et al. | |
| 7,073,510 B2 | 7/2006 | Redmond et al. | |
| 7,131,951 B2 | 11/2006 | Angel | |
| 8,128,639 B2 | 3/2012 | Tippett | |
| 8,209,006 B2 | 6/2012 | Smith et al. | |
| 8,246,611 B2 | 8/2012 | Paithankar et al. | |
| 8,435,791 B2 | 5/2013 | Galun et al. | |
| 8,480,592 B2 | 7/2013 | Chudzik et al. | |
| 9,439,673 B2 | 9/2016 | Austen | |

| | | | |
|---|---|---|---|
| 2002/0169431 A1 | 11/2002 | Kline et al. | |
| 2003/0088220 A1 | 5/2003 | Molander et al. | |
| 2003/0119641 A1 | 6/2003 | Reising | |
| 2003/0153960 A1 * | 8/2003 | Chornenky | A61N 1/0502 |
| | | | 607/72 |
| 2003/0158521 A1 | 8/2003 | Ameri | |
| 2003/0233082 A1 | 12/2003 | Kline et al. | |
| 2004/0019297 A1 * | 1/2004 | Angel | A61B 10/04 |
| | | | 600/564 |
| 2004/0023771 A1 | 2/2004 | Reising et al. | |
| 2004/0073195 A1 | 4/2004 | Cucin | |
| 2005/0090765 A1 | 4/2005 | Fisher | |
| 2005/0130821 A1 | 6/2005 | Reising et al. | |
| 2005/0165329 A1 | 7/2005 | Taylor et al. | |
| 2005/0209567 A1 | 9/2005 | Sibbitt, Jr. | |
| 2005/0215921 A1 | 9/2005 | Hibner et al. | |
| 2005/0215970 A1 | 9/2005 | Kline et al. | |
| 2005/0215971 A1 | 9/2005 | Roe et al. | |
| 2005/0234419 A1 | 10/2005 | Kline et al. | |
| 2005/0245952 A1 | 11/2005 | Feller | |
| 2005/0283141 A1 | 12/2005 | Giovannoli | |
| 2006/0064031 A1 | 3/2006 | Miller | |
| 2006/0116605 A1 | 6/2006 | Nakao | |
| 2006/0161179 A1 | 7/2006 | Kachenmeister | |
| 2006/0184153 A1 | 8/2006 | Mark et al. | |
| 2006/0259006 A1 | 11/2006 | McKay et al. | |
| 2007/0038181 A1 | 2/2007 | Melamud et al. | |
| 2007/0060888 A1 | 3/2007 | Goff et al. | |
| 2007/0073217 A1 | 3/2007 | James | |
| 2007/0073327 A1 | 3/2007 | Giovannoli | |
| 2007/0078466 A1 | 4/2007 | Bodduluri et al. | |
| 2007/0078473 A1 | 4/2007 | Bodduluri et al. | |
| 2007/0106306 A1 | 5/2007 | Bodduluri et al. | |
| 2007/0156161 A1 | 7/2007 | Weadock et al. | |
| 2007/0179455 A1 | 8/2007 | Geliebter et al. | |
| 2007/0183938 A1 | 8/2007 | Booker | |
| 2007/0198000 A1 | 8/2007 | Miyamoto et al. | |
| 2007/0213634 A1 | 9/2007 | Teague | |
| 2007/0239260 A1 | 10/2007 | Palanker et al. | |
| 2007/0249960 A1 | 10/2007 | Williamson, IV | |
| 2007/0270710 A1 | 11/2007 | Frass et al. | |
| 2008/0009802 A1 | 1/2008 | Lambino et al. | |
| 2008/0009896 A1 * | 1/2008 | Shiao | A61B 17/3468 |
| | | | 606/187 |
| 2008/0009901 A1 | 1/2008 | Redmond et al. | |
| 2008/0045858 A1 | 2/2008 | Tessitore et al. | |
| 2008/0132979 A1 | 6/2008 | Gerber | |
| 2008/0234602 A1 | 9/2008 | Oostman et al. | |
| 2008/0234699 A1 | 9/2008 | Oostman, Jr. et al. | |
| 2008/0300507 A1 | 12/2008 | Figueredo et al. | |
| 2008/0312648 A1 | 12/2008 | Peterson | |
| 2009/0030340 A1 | 1/2009 | McClellan | |
| 2009/0088720 A1 * | 4/2009 | Oostman, Jr. | A61B 34/30 |
| | | | 604/403 |
| 2009/0227895 A1 | 9/2009 | Goldenberg | |
| 2009/0312749 A1 | 12/2009 | Pini et al. | |
| 2010/0023003 A1 | 1/2010 | Mulholland | |
| 2010/0030152 A1 * | 2/2010 | Lee | A61M 37/0015 |
| | | | 604/131 |
| 2010/0082042 A1 | 4/2010 | Drews | |
| 2010/0121307 A1 | 5/2010 | Lockard et al. | |
| 2010/0160822 A1 | 6/2010 | Parihar et al. | |
| 2010/0185116 A1 | 7/2010 | Al-Mohizea | |
| 2010/0286618 A1 * | 11/2010 | Choi | A61M 5/32 |
| | | | 604/173 |
| 2010/0330589 A1 | 12/2010 | Bahrami et al. | |
| 2011/0028898 A1 * | 2/2011 | Clark, III | A61B 17/32002 |
| | | | 604/151 |
| 2011/0105949 A1 | 5/2011 | Wiksell | |
| 2011/0245834 A1 | 10/2011 | Miklosovic | |
| 2011/0251602 A1 | 10/2011 | Anderson et al. | |
| 2011/0282238 A1 | 11/2011 | Houser et al. | |
| 2011/0313345 A1 * | 12/2011 | Schafer | A61B 17/22012 |
| | | | 604/22 |
| 2011/0313429 A1 | 12/2011 | Anderson et al. | |
| 2012/0041430 A1 | 2/2012 | Anderson et al. | |
| 2012/0136387 A1 | 5/2012 | Redmond et al. | |
| 2012/0226214 A1 | 9/2012 | Gurtner et al. | |

(56) References Cited

U.S. PATENT DOCUMENTS

| | | |
|---|---|---|
| 2012/0226306 A1 | 9/2012 | Jackson et al. |
| 2012/0253333 A1 | 10/2012 | Garden et al. |
| 2012/0271320 A1 | 10/2012 | Hall et al. |
| 2013/0045171 A1 | 2/2013 | Utecht et al. |
| 2014/0200484 A1 | 7/2014 | Austen et al. |
| 2014/0277055 A1 | 9/2014 | Austen, Jr. |
| 2014/0296741 A1 | 10/2014 | Austen |
| 2016/0095592 A1 | 4/2016 | Levinson et al. |
| 2016/0367280 A1 | 12/2016 | Austen |

FOREIGN PATENT DOCUMENTS

| | | |
|---|---|---|
| CN | 101208128 A | 6/2008 |
| CN | 101232858 A | 7/2008 |
| CN | 101347346 A | 1/2009 |
| DE | 202004010659 U1 | 10/2004 |
| EA | 9092 B1 | 10/2007 |
| EP | 0027974 A1 | 5/1981 |
| EP | 1224949 A1 | 7/2002 |
| EP | 1396230 A1 | 3/2004 |
| EP | 1278061 B1 | 2/2011 |
| EP | 2409727 A1 | 1/2012 |
| JP | 2005000642 A | 1/2005 |
| JP | 2005103276 A | 4/2005 |
| JP | 2009219858 S | 10/2009 |
| JP | 2010515469 A | 5/2010 |
| JP | 2010532178 A | 10/2010 |
| KR | 20100135864 A | 12/2010 |
| RU | 2119304 C1 | 9/1998 |
| RU | 11679 U1 | 11/1999 |
| RU | 28328 U1 | 3/2003 |
| RU | 50799 U1 | 1/2006 |
| RU | 58359 U1 | 11/2006 |
| RU | 2308873 C2 | 10/2007 |
| SU | 1426740 A1 | 9/1988 |
| SU | 1801391 A1 | 8/1990 |
| WO | 9322971 A1 | 11/1993 |
| WO | 9929243 A1 | 6/1999 |
| WO | 0141651 A2 | 6/2001 |
| WO | 2006118804 A1 | 11/2006 |
| WO | 2007011788 A2 | 1/2007 |
| WO | 2007024038 A1 | 3/2007 |
| WO | 2007106170 A2 | 9/2007 |
| WO | 2009072711 A2 | 6/2009 |
| WO | 2009099988 A2 | 8/2009 |
| WO | 2009137288 A2 | 11/2009 |
| WO | 2009146053 A1 | 12/2009 |
| WO | 2009146068 A1 | 12/2009 |
| WO | 2010027188 A2 | 3/2010 |
| WO | 2010080014 A2 | 7/2010 |
| WO | 2010097790 A1 | 9/2010 |
| WO | 2012052986 A1 | 4/2012 |
| WO | 2012103483 A2 | 8/2012 |
| WO | 2012103488 A1 | 8/2012 |
| WO | 2012103492 A1 | 8/2012 |
| WO | 2012119131 A1 | 9/2012 |
| WO | 2012135828 A1 | 10/2012 |
| WO | 2013013196 A1 | 1/2013 |
| WO | 2013013199 A2 | 1/2013 |
| WO | 2014179729 A1 | 11/2014 |
| WO | 2015021434 A2 | 2/2015 |

OTHER PUBLICATIONS

Cevc, Review—Biologicals & Immunologicals—Drug Delivery Across the Skin, Expert Opinion on Investigational Drugs, 1997, 6(12):1887-1888.
Chang, An Updated Review of Tyrosinase Inhibitors, International Journal of Molecular Sciences, 2009, 10:2440-2475.
Czech, et al., Pressure-Sensitive Adhesives for Medical Applications, INTECH Open Access Publisher, 2011, pp. 309-332.
Dai, et al., Magnetically-Responsive Self Assembled Composites, Chemical Society Reviews, 2010, 39:4057-4066.
De Las Heras Alarcon, et al., Stimuli Responsive Polymers for Biomedical Applications, Chemical Society Reviews, 2005, 34:276-285.
Dini, et al., Grasping Leather Plies by Bernoulli Grippers, CIRP Annals—Manufacturing Technology, 2009, 58:21-24.
Dujardin, et al., In Vivo Assessment of Skin Electroporation Using Square Wave Pulses, Journal of Controlled Release, 2002, 79:219-227.
Fernandes, et al., Micro-Mechanical Fractional Skin Rejuvenation, Plastic and Reconstructive Surgery, 2012, 130(5S-1): 28.
Fernandes, et al., Micro-Mechanical Fractional Skin Rejuvenation, Plastic and Reconstructive Surgery, 2013, 131:216-223.
Galaev, 'Smart' Polymers in Biotechnology and Medicine, Russian Chemical Reviews, 1995, 64(5):471-489.
Glogau, Aesthetic and Anatomic Analysis of the Aging Skin, Seminars in Cutaneous Medicine and Surgery, 1996, 15(3):134-138.
Hale, et al., Optical Constants of Water in the 200-nm to 200-μm Wavelength Region, Applied Optics, 1973, 12(3):555-563.
Huang, et al., Shape Memory Materials, Materials Today, 2010, 13(7):54-61.
Kakasheva-Mazenkovska, et al., Variations of the Histomorphological Characteristics of Human Skin of Different Body Regions in Subjects of Different Age, Contributions/Macedonian Academy of Sciences and Arts, Section of Biological and Medical Sciences, 2010 32(2):119-128.
Konermann, et al., Ultrasonographically Guided Needle Biopsy of Benign and Malignant Soft Tissue and Bone Tumors, Journal of Ultrasound in Medicine, 2000, 19(7):465-471.
Lien, et al., A Novel Gripper for Limp Materials Based on Lateral Coanda Ejectors, CIRP Annals—Manufacturing Technology, 2008, 57:33-36.
Majid, Microneedling Therapy in Atrophic Facial Scars: An Objective Assessment, Journal of Cutaneous and Aesthetic Surgery, 2009, 2(1):26-30.
Pliquett, et al., A Propagating Heat Wave Model of Skin Electroporation, Journal of Theoretical Biology, 2008, 251:195-201.
Prausnitz, et al., Electroporation of Mammalian Skin: A Mechanism to Enhance Transdermal Drug Delivery, Proc. Natl. Acad. Sci., 1993, 90:10504-10508.
European Patent Office, Extended European Search Report, Application No. 12814711.3, dated Feb. 11, 2015.
PCT International Search Report and Written Opinion, PCT/US2012/047708, dated Oct. 18, 2012.
PCT International Search Report and Written Opinion, PCT/US2014/036638, dated Oct. 2, 2014.
PCT International Preliminary Report on Patentability, PCT/US2014/036638, dated Nov. 3, 2015.
PCT International Search Report and Written Opinion, PCT/US2014/050426, dated Feb. 4, 2015.
PCT International Preliminary Report on Patentability, PCT/US2014/050426, dated Feb. 9, 2016.
Bolshaya meditsinskaya entsiklopediya, M., 1976, vol. 3, p. 184.
Bolshaya meditsinskaya entsiklopediya, M., 1986, vol. 27, pp. 480-481.
European Patent Office, Supplementary European Search Report, Application No. 12738813, dated Jun. 12, 2014.
PCT International Search Report and Written Opinion, PCT/US2012/022980, dated Aug. 9, 2012.
PCT International Search Report and Written Opinion, PCT/US2012/022993, dated May 17, 2012.
PCT International Search Report and Written Opinion, PCT/US2012/047716, dated Oct. 25, 2012.
Spravochik operatsionnoy I perevyazochnoy sestrie, M., <<Meditsina>>, 1985, p. 31.

* cited by examiner

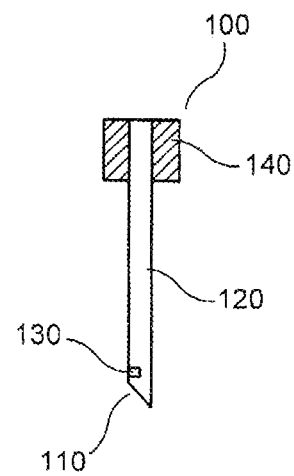 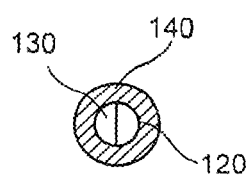 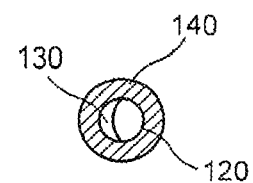
F I G. 1A             F I G. 1B            F I G. 1C
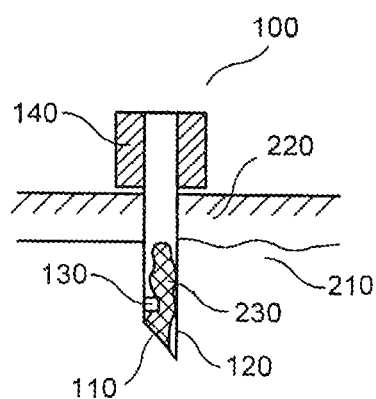 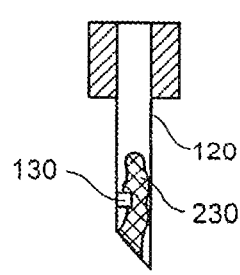 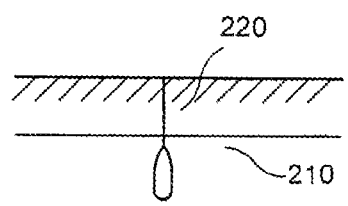
F I G. 2A             F I G. 2B            F I G. 2C

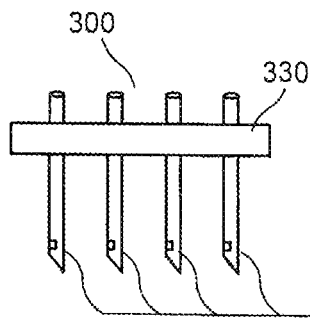
F I G. 3A
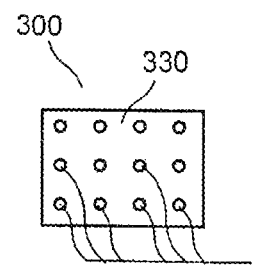
F I G. 3B
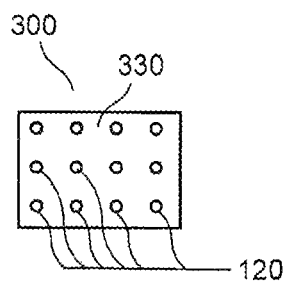
F I G. 3C
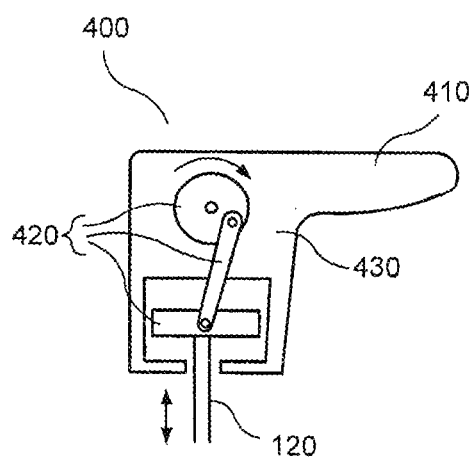
F I G. 4

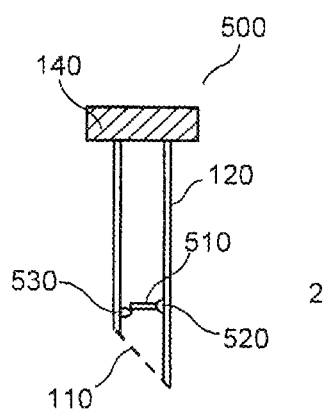 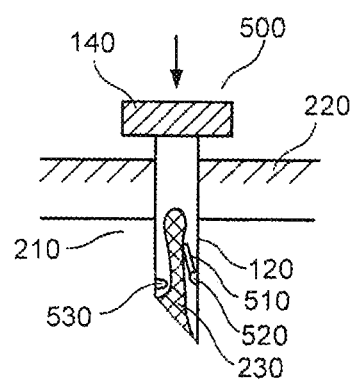 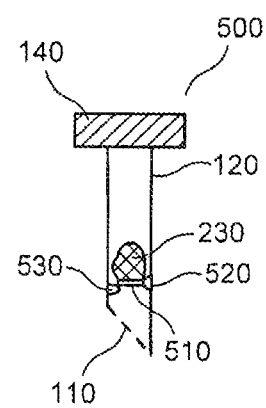
FIG. 5A  FIG. 5B  FIG. 5C
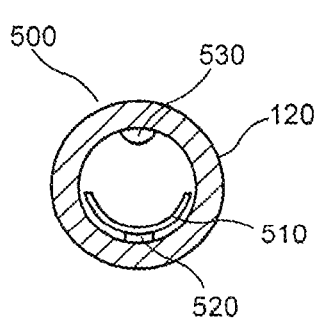 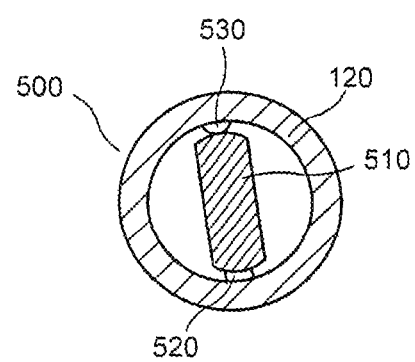
FIG 6A  FIG. 6B

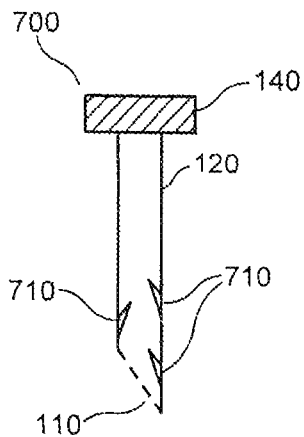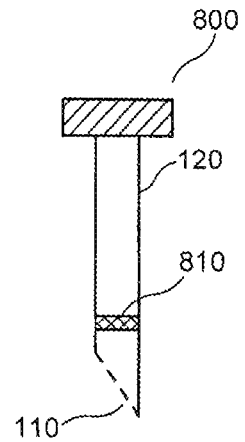
FIG. 7  FIG. 8A
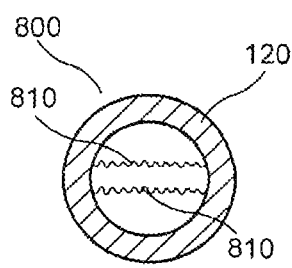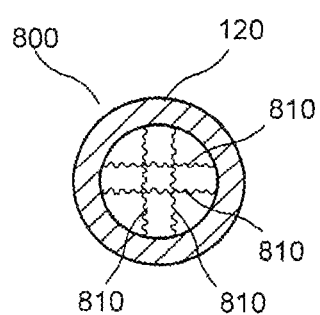
FIG. 8B  FIG. 8C

METHOD AND APPARATUS FOR DAMAGE AND REMOVAL OF FAT

CROSS REFERENCE TO RELATED APPLICATIONS

The present application is a division of U.S. patent application Ser. No. 14/233,985 filed on Jun. 3, 2014 which is a U.S. National Stage of PCT Application No. PCT/US2012/047708 filed on Jul. 20, 2012 which relates to and claims priority from U.S. Provisional Patent Application Ser. No. 61/510,242 filed Jul. 21, 2011, the disclosure of which is incorporated herein by reference in its entirety.

FIELD OF THE DISCLOSURE

The present disclosure relates to methods and apparatus for removing or damaging small regions of fatty tissue, e.g., subcutaneous fat, while reducing or avoiding significant damage to the overlying tissue, e.g., the dermis and epidermis.

BACKGROUND INFORMATION

Procedures and devices for removing fatty tissue, e.g. for cosmetic reasons, are common and represent a significant market in the cosmetic procedures sector. Conventional fat-removal procedures and devices, e.g., liposuction, can be disruptive to surrounding tissue and often includes many risks such as excessive bleeding, etc. There are relatively few procedures for removal of small amounts of fatty tissue, e.g., subcutaneous fat, for cosmetic purposes and such procedures generally require a skilled practitioner for effective removal and can be very time-consuming and subject to complications.

Accordingly, there may be a need to provide simpler and safer method and apparatus for removal of subcutaneous fatty tissue that addresses and/or reduces the limitations described above.

SUMMARY OF THE DISCLOSURE

The present disclosure describes exemplary embodiments of simple, inexpensive, and safe methods and devices for affecting fatty tissue, e.g., subcutaneous fat, while reducing or avoiding significant damage to the overlying tissue, such as the dermis and epidermis. Such methods and apparatus can provide removal of small portions of subcutaneous fatty tissue, which may optionally be implanted in other parts of the body or used to harvest stem cells present therein. Methods and apparatus for locally disrupting small regions of fatty tissue, which may then be resorbed by the body, are also described.

An exemplary apparatus according to the present disclosure can be provided that includes a hollow needle and at least one protrusion provided on an inner wall of the hollow needle. The hollow needle can be configured to be inserted into a biological tissue such as skin, such that the needle penetrates the upper tissue layers. The size and geometry of the needle can be configured such that softer or less resilient subsurface tissue, e.g., subcutaneous fat, can enter the hollow core of the needle when the distal end of the needle advances into the fat. The protrusion can be configured to facilitate retention of a portion of the fat when the needle is withdrawn from the tissue.

In a further exemplary embodiment of the present disclosure, a plurality of such hollow needles that include internal protrusions can be affixed to a substrate. The substrate and needles can be arranged to control and/or limit the depth of penetration of the needles into the tissue when the substrate is placed on the tissue surface. For example, the lengths of the distal ends of the needles protruding from a lower surface of the substrate can be selected to correspond to a depth within the fatty tissue below the skin surface.

In further exemplary embodiments of the present disclosure, the hollow needle can include a pivoting flap or one or more barbs provided within the lumen to facilitate detachment and removal of portions of the fat by the needle.

In yet further exemplary embodiments of the present disclosure, the hollow needle can include a cutting arrangement provided within the lumen to facilitate mechanical damage and/or disruption of portions of the fat by the needle.

In a another exemplary embodiment of the present disclosure, the exemplary apparatus can further include a vacuum source provided in communication with the proximal ends of the needles, which can facilitate separation and/or removal of portions of the fat from the surrounding tissue when the needle is inserted and withdrawn.

In a still further exemplary embodiment of the present disclosure, the exemplary apparatus can include a reciprocating arrangement affixed to the one or more needles. The reciprocating arrangement can include a motor or other actuator configured to repeatedly advance and withdraw the needles relative to the tissue. The reciprocating arrangement can be provided in a housing that facilitates manipulation of the apparatus, e.g., placement of the apparatus on the tissue being treated and/or traversing the apparatus over the tissue. The housing can optionally be configured to stretch or otherwise stabilize the tissue proximal to the needle(s) being inserted, to reduce deformation of the tissue and/or improve accuracy of the placement of the needle(s) in the tissue. The reciprocating arrangement can further include a translational controller configured to translate the needles over the tissue in at least one direction, and optionally in two orthogonal directions, to facilitate removal or harvesting of fat from larger regions of a donor tissue site without translating the entire apparatus over the tissue surface.

In yet another exemplary embodiment of the present disclosure, the exemplary apparatus can include a vibrating arrangement mechanically coupled to the one or more needles. The vibrating arrangement can facilitate improved removal and/or disruption of the fat tissue by the needles.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which:

FIG. 1A is a cross-sectional side view of an exemplary apparatus for removal of subsurface fatty tissue in accordance with exemplary embodiments of the present disclosure;

FIG. 1B is a lateral cross-sectional view of the exemplary apparatus shown in FIG. 1A according to a first embodiment of the present disclosure;

FIG. 1C is a lateral cross-sectional view of the exemplary apparatus shown in FIG. 1A according to a second embodiment of the present disclosure;

FIGS. 2A-2C are schematic side views of the exemplary apparatus shown in FIG. 1A being used to remove subsurface fatty tissue in accordance with exemplary embodiments of the present disclosure;

FIG. 3A is a cross-sectional side view of a second exemplary apparatus for removal of subsurface fatty tissue in accordance with further exemplary embodiments of the present disclosure;

FIG. 3B is a schematic frontal view of a first exemplary embodiment of the exemplary apparatus shown in FIG. 3A;

FIG. 3C is a schematic frontal view of a second exemplary embodiment of the exemplary apparatus shown in FIG. 3A;

FIG. 4 is a cross-sectional side view of a third exemplary apparatus for removal of subsurface fatty tissue in accordance with still further exemplary embodiments of the present disclosure;

FIG. 5A is a cross-sectional side view of a fourth exemplary apparatus for removal of subsurface fatty tissue in accordance with still further exemplary embodiments of the present disclosure;

FIGS. 5B and 5C are schematic side views of the exemplary apparatus shown in FIG. 5A illustrating removal of subsurface fatty tissue in accordance with exemplary embodiments of the present disclosure;

FIG. 6A is a view of one end of a first exemplary embodiment of the exemplary apparatus shown in FIG. 5A;

FIG. 6B is a view of one end of a second exemplary embodiment of the exemplary apparatus shown in FIG. 5A;

FIG. 7 is a cross-sectional side view of a fifth exemplary apparatus for removal of subsurface fatty tissue in accordance with still further exemplary embodiments of the present disclosure;

FIG. 8A is a cross-sectional side view of an exemplary apparatus for damage or disruption of subsurface fatty tissue in accordance with yet further exemplary embodiments of the present disclosure;

FIG. 8B is a view of one end of a first exemplary variant of the exemplary apparatus shown in FIG. 8A; and FIG. 8C is a view of one end of a second exemplary variant of the exemplary apparatus shown in FIG. 8A.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION

Exemplary embodiments of the present disclosure can provide a method and apparatus for removing or locally damaging or disrupting soft tissue, e.g., subcutaneous fat, while reducing or avoiding significant damage to the overlying tissue, e.g., the dermis and epidermis in skin. Exemplary embodiments of the present disclosure can thereby facilitate removal, harvesting or disruption of subsurface tissue while avoiding and/or minimizing adverse effects such as scarring, bleeding, likelihood of infection, etc.

A cross-sectional view of an exemplary apparatus 100 for removing fatty tissue is shown in FIG. 1A. The exemplary apparatus 100 can include a hollow needle 120 having a central lumen that further includes at least one protrusion 130 provided along at least a portion of an inner surface thereof, e.g., extending into a portion of the central lumen. An open distal end 110 of the needle 120 can be provided with a sharpened and/or angled edge to facilitate insertion of the needle 120 into skin or other tissue. For example, the distal end 110 of the needle 120 can be provided as a wedge shape that can be formed, e.g., by grinding the end of the needle 120 at an acute angle relative to its longitudinal axis. The angle of the distal end can be, e.g., approximately 45 degrees, or between about 30 degrees and about 50 degree, which can provide the tissue-selective penetration characteristics described herein. These exemplary angles can be used with any of the exemplary embodiments described herein.

The protrusion 130 can be provided along the inner surface of a shorter side of the angled or tapered end 110 of the needle 120. A handle 140 and/or other gripping arrangement can be provided at a proximal portion of the needle 120 to facilitate holding and manipulating the needle 120.

A frontal view of the exemplary apparatus 100 is shown in FIG. 1B. The protrusion 130 can be configured to block and/or occlude a portion of the hollow center of the needle 120. The exemplary protrusion 130 shown in FIG. 1B can include a substantially straight edge provided towards the center of the hollow core of the needle 120. A further exemplary protrusion 130 is shown in FIG. 1C that includes a curved edge oriented towards the center of the hollow core of the needle 120. Other shapes for the protrusion 130 can also be used in further exemplary embodiments of the present disclosure. A plurality of such protrusions 130 can also be provided in the needle 120. The cross-sectional shape of the exemplary needle 120 shown in FIG. 1B is substantially round. The needles 120 having other cross-sectional shapes can also be used, e.g., needles 120 can be provided that have oval, square, or triangular cross-sections, etc.

For example, the protrusion 130 can block less than about 50% of the cross-sectional area of the hollow center, or optionally less than about 30% of this area. The protrusion 130 can block more than about 10% of the cross-sectional area, or more than about 20% of this area. The size and shape of the protrusion 130 can be configured to facilitate a retention of fatty tissue in the hollow core of the needle 120 as described herein.

The exemplary apparatus 100 can be inserted into a dermal tissue such that the distal end 110 penetrates at least partially into the subcutaneous fatty layer 210 beneath the dermis 220, as shown in FIG. 2. A portion 230 of the fatty tissue can be present within the hollow core of the needle 120 after such insertion. The exemplary apparatus 100 can then be withdrawn from the dermal tissue. As shown in FIG. 2B, the portion 230 of the fatty tissue can also be removed from the fatty layer 210, and can remain inside the hollow needle 210. The protrusion 130 can facilitate the removal of the portion 230 of the fatty tissue from the fatty layer 210. After the removal of the exemplary apparatus 100 from the dermal tissue, the dermal layer can collapse around the insertion path, as shown in FIG. 2C, and subsequently heal, whereas a portion 230 of fat from the fatty layer 210 has been removed. Accordingly, such exemplary method and apparatus can facilitate the removal of the subcutaneous fat 230 with a relatively little disturbance of the overlying dermis 220.

The diameter of the needle 120 can be selected to facilitate the insertion through the dermal layer 220 without removing a substantial amount of the dermal tissue, as well as separation and removal of the portion 230 of the fatty tissue, as described herein. For example, the needle 120 can have the size of a conventional 16 gauge needle, or between 14 gauge and 19 gauge. Such needle diameters can provide the tissue-selective penetration properties described herein when the apparatus 100 is inserted into skin. The diameter of the central lumen of the needle 120 can be, e.g., about 1 mm or about 1.25 mm. These exemplary needle sizes can be used with any of the exemplary embodiments described herein. Larger or smaller needle sizes may also be used in embodiments of the present disclosure if they exhibit the selective tissue properties described herein, e.g., if the methods and apparatus described herein are being used on tissues other than skin.

In exemplary embodiments of the present disclosure, the angled or tapered distal end 110 of the needle 120 as described herein can divert or push aside the resilient dermal tissue 220 as the needle 120 is inserted. As the needle 120 penetrates further into the fatty layer 210, the portion 230 of the softer fatty tissue can be more easily separated from the surrounding fatty layer 210, and enter the hollow core of the needle 120. The protrusion 130 can anchor the portion 230 of fatty tissue within the needle 120, and facilitate its separation and removal from the surrounding fatty layer 210 when the exemplary apparatus 100 is withdrawn from the dermal tissue. The exemplary apparatus 100 can be inserted and removed a plurality of times to remove further portions 230 of the fatty tissue.

A further exemplary apparatus 300 for removal of subcutaneous fat according to the present disclosure is shown in FIG. 3A. This exemplary apparatus 300 can include a plurality of needles 120 affixed to a substrate 330. The substrate 330 can have a substantially flat lower surface from which the needles 120 protrude, or this surface may be curved or otherwise contoured, e.g., to more closely match a contour of the surface of the dermal tissue being treated.

A frontal view of the exemplary apparatus 300 is shown in FIG. 3B. The needles 120 can be arranged in a square or rectangular pattern, as shown in FIG. 3B. Alternatively, the rows of needles 120 can be offset or staggered to form a triangular pattern, as shown in FIG. 3C. Other exemplary arrangements of needles 120 can also be used, such as a spatially random distribution of the needles 120 on the substrate 330. The number of the needles 120 and spacing between adjacent ones of the needles 120 can be selected based on the particular tissue being treated, the amount of fat to be removed, etc.

The protrusion distance of the needles 120 from the lower surface of the substrate 330 can also be selected based on a local depth of the subcutaneous fatty layer 210 and the depth to which the fatty tissue is to be removed. For example, the exemplary apparatus 300 can include an arrangement configured to adjust the protrusion distance of the needles 120. Such arrangement can include, e.g., a plate or the like affixed to the substrate 330 such that the needles 120 pass through the plate. The distance between the plate and the substrate 330 can be adjustable to vary the distance that the needles 120 protrude from the lower surface of the plate. Other exemplary arrangements that can facilitate the adjustment of the effective length of the needles 120 protruding from the bottom of the apparatus 300 may also be used. The location of the one or more protrusions 130 within the needles 120 can also be selected to control the size or height of the tissue samples 230 that may be retained and removed in the needles 120 when they are inserted into and withdrawn from the tissue, as described herein.

The exemplary apparatus 300 can be pressed into the dermal tissue and subsequently withdrawn, such that the needles 120 penetrate into the into the fatty layer 210 and remove portions of the tissue sample 230 of the fatty tissue from the fatty layer 210, as described herein and shown in FIGS. 2A-2C for a single needle 210. The exemplary apparatus 300 can facilitate removal or harvesting of a larger amount of fatty tissue with a single insertion and withdrawal of the exemplary apparatus 300 from the dermal tissue.

A still further exemplary apparatus 400 according to the present disclosure is shown in FIG. 4 that includes one or more needles 120 as described herein, which can be affixed to a reciprocating arrangement 420 provided within a housing 430. The housing 430 can also include a handle 410. The reciprocating arrangement 420 can be configured to displace the needle 120 hack and forth along a direction that can be substantially parallel to the axis of the needle 120. For example, the reciprocating arrangement 420 can be powered by a motor or the like, and/or controlled by a switch that can turn the reciprocating arrangement 420 on and off, and can further control the reciprocating frequency and/or protrusion distance of the needle 120 below the lower surface of the housing 430. The exemplary apparatus 400 can be traversed over a region of skin to be treated such that the one or more needles 120 can be repeatedly inserted and withdrawn from the tissue, removing a portion of fatty tissue upon each withdrawal as described herein. The penetration depth of the needles 120 can be determined by the configuration of the reciprocating arrangement 420.

In a further exemplary embodiment according to the present disclosure, the reciprocating arrangement 420 can further include a translational mechanism configured to translate the one or more needles 120 over the tissue surface in one or two orthogonal directions. For example, the reciprocating arrangement 420 can be configured to translate such one or more needles 120 over an area of the tissue while the exemplary apparatus 400 is held stationary with respect to the tissue surface at a donor or treatment site. In one exemplary embodiment of the present disclosure, the reciprocating arrangement 420 can be configured to translate the one or more needles 120 along a single direction to harvest fatty tissue along one or more rows. The exemplary apparatus 400 can optionally be translated over the tissue surface after such rows are formed, e.g., in a direction that is not parallel to the row, to remove or harvest fatty tissue from a larger area of the donor tissue site.

In further exemplary embodiments of the present disclosure, any of the exemplary apparatuses described herein can be configured to remove or harvest fatty tissue from a plurality of locations in any of a variety of spatial distributions, where each location can correspond to a single insertion and withdrawal of a single needle 120. For example, the fatty tissue can be removed or harvested from a plurality of locations configured as one or more rows, a regular two-dimensional pattern, a random distribution, or the like. Such exemplary patterns or spatial distributions of fat harvesting or removal sites can be generated based on, e.g., the configuration of such one or more needles 120 provided, the properties of the reciprocating arrangement 420, and/or the rate of translation of the exemplary apparatus 400 over the tissue surface.

In still further exemplary embodiments according to the present disclosure, the housing 430 can be configured to stretch skin or other tissue when the exemplary apparatus 400 is placed on the tissue to be treated. Such stretching can facilitate mechanical stabilization of the tissue, e.g., to reduce or avoid deformation of the tissue 350 while the needles 120 are inserted into and withdrawn from the tissue. Such stretching of the tissue can also reduce the effective size of the disrupted region of the upper tissue layers formed by the exemplary apparatus 400 when the tissue is allowed to relax after treatment. Alternatively, the surface of the tissue to be treated can be stretched or stabilized using other techniques prior to and/or during treatment of the region in accordance with any of the exemplary embodiments described herein.

For example, a vacuum or suction source, e.g. a pump or a reservoir containing a fluid under low-pressure, can be provided in communication with the lumen of the needle 120, e.g., via a conduit in communication with the proximal end of the needles 120, in any of the exemplary embodiments described herein. Such low pressure, e.g., pressure less than atmospheric or ambient pressure, provided in the central lumen can facilitate the removal of the portions 230 of fatty tissue when the distal ends of the needles 120 are located within the subcutaneous fat layer 210. For example, the exemplary devices described herein can be configured to provide such a vacuum when the distal ends of the needles 120 are at least partially inserted into the fatty layer 210, and such vacuum may be applied as the needles 120 are withdrawn from the fatty layer 210. The strength of the vacuum can be selected to facilitate removal of the portions 230 of the fatty tissue within the distal portions of the needles 120, without causing a significant damage to the tissue surrounding the inserted needles 120.

In another exemplary embodiment of the present disclosure, an apparatus 500 can be provided that is adapted to remove fatty tissue is shown in FIG. 5A. The exemplary apparatus 500 can include a hollow needle 120 having a central lumen, where the size and shape of the needle 120 and distal end 110 thereof can be similar to those described herein above for the apparatus 100 shown in FIG. 1A. The apparatus 500 can include at least one pivoting flap 510 within the lumen of the needle 120. The flap 510 can be provided in the distal portion of the needle 120, e.g., and configured such that one portion of the flap 510 is pivotally connected to an inside wall of the needle 120 at a pivot point 520.

A stop arrangement 530 can be provided on another location on the inside wall of the needle 120 to constrain or prevent movement of the flap beyond a certain limit in a particular direction. For example, the stop arrangement 530 can be provided on an opposite side of the interior needle wall from the pivot point 520, as shown in FIG. 5A. In this exemplary configuration, the flap 510 can be free and configured to pivot upwards towards the proximal end of the needle 120, but may be constrained from pivoting towards the distal end 110 of the needle 120 past the stop arrangement 530. In further exemplary embodiments, the stop arrangement 530 can be provided at a location further up or down from the pivot point 520 (e.g., closer to or further from the distal end 110 of the needle 120). The stop arrangement 530 can also be provided on a lateral side of the interior needle wall, instead of diametrically opposite the pivot point 520 as illustrated in FIG. 5A. The stop arrangement 530 can be provided, e.g., by indenting an exterior portion of the needle wall such that the portion of the wall projects or bulges inward into the lumen of the needle 120. Alternatively, a small object can be affixed to the interior wall of the needle 120 to form the stop arrangement. Other techniques and configurations may also be used to provide the stop arrangement 530.

The exemplary apparatus 500 can be used to remove or harvest portions of fatty tissue in a manner similar to that described with respect to the exemplary apparatus 100 and shown in FIGS. 2A-2C. For example, the distal end 110 of the apparatus 500 can be advanced through the dermis 220 and into the subcutaneous fat layer 210, as shown in FIG. 5B. The exemplary apparatus 500 can be configured such that the distal end penetrates the dermis 220 with little or no portion of the dermal tissue entering the lumen of the needle 120. As the distal end 110 penetrates the fat layer 210, a portion 230 of softer fatty tissue may enter the lumen of the needle 120. The portion 230 can advance into the lumen, pushing the flap 510 upward and closer to the inner wall of the needle 120, as shown in FIG. 5B.

When the exemplary apparatus 500 is withdrawn from the skin, the fat portion 230 may be pulled downward slightly within the lumen, pulling or dragging the flap 510 with it towards the distal end 110 of the needle 120. For example, an edge of the flap 510 may 'catch' or penetrate the edge of the fat portion 230. As the flap 510 moves downward, it may partially or completely sever the fat portion 230 from the remainder of the subcutaneous fat below it, thereby retaining the fat portion 230 within the apparatus 500 as the apparatus 500 is withdrawn from the skin.

The flap 510 can be substantially round or moon shaped, e.g., such that it can block or occlude substantially the entire lumen when it is lowered against the stop arrangement 530. For example, an exemplary flap 510 is illustrated in FIG. 6A in a raised position (e.g., pivoted upward away from the distal end 110 of the needle 120). In this figure, the view of the flap 510 is from the distal end 110 of the needle 120 along the longitudinal axis thereof. In this exemplary configuration, the thin round flap is curved rather than planar, such that it can more closely conform to the shape of the inner wall of the needle 120 when pivoted upward as shown in FIG. 6A. Such a curved flap 510 can facilitate advancement of a fatty tissue 230 into the exemplary apparatus 500 by reducing or minimizing obstruction of the lumen when it is pivoted upward.

In a further exemplary embodiment, the flap 510 can be provided as a substantially rectangular shape or in another shape that does not fully occlude the lumen when the flap 510 is pivoted to a lowered position, e.g., resting against the stop arrangement 530, as shown in a view of an end the needle 120 in FIG. 6B. This exemplary flap shape can also be curved, similar to the flap 510 shown in FIG. 6A, to reduce obstruction of the lumen when the flap 510 is pivoted in an upward position.

Any of the features of the exemplary apparatus 500 can be used in conjunction with the other exemplary embodiments described herein. For example, one or more needles 120 that include a pivoting flap 510, and the stop arrangement 530 can be affixed to a substrate 330, e.g., as shown in FIGS. 3A-3C. One or more such needles 120 that include a pivoting flap 510 can also be coupled to a reciprocating arrangement 420 as illustrated in FIG. 4.

In a still further exemplary embodiment of the present disclosure, an apparatus 700 can be provided that includes one or more barbs 710 provided on the interior wall of the hollow needle 120. The barb 710 can be angled upward, e.g., sloping away from the distal end 110 of the needle 120, as shown in FIG. 7. Such exemplary configuration can facilitate an advancement of fatty tissue into the lumen as the apparatus 700 is advanced into the fat layer 210, while promoting retention of a fat portion 230 within the lumen as the apparatus 700 is withdrawn from the skin. Such barbs can be formed, e.g., by deforming the outer wall of the needle 120 inward at an angle at one or more locations, by attaching pre-formed barbs 710 to the inside wall of the needle 120, or by other techniques. The features of the exemplary apparatus 700 can be used in conjunction with the other exemplary embodiments described herein. For example, a plurality of needles 120 that include one or more barbs 710 can be affixed to a substrate 330, e.g., as shown in FIGS. 3A-3C. One or more such needles 120 can also be coupled to a reciprocating arrangement 420 as illustrated in FIG. 4.

In further exemplary embodiments of the present disclosure, an apparatus 800 can be provided that includes a cutting arrangement 810 provided in a distal portion of the lumen of the hollow needle 120, as shown in FIG. 8A. The apparatus 800 can facilitate mechanical disruption of fatty tissue 210 without removing a substantial amount thereof from the surrounding tissue. As with the other exemplary embodiments described herein, the exemplary apparatus 800 can affect tissue in the fat layer 210 without significantly affecting or damaging the overlying dermal layer 220 when the apparatus 800 is withdrawn from the skin. For example, a generation of mechanical disruption in the fat layer 210 can lead to cellular damage and/or death. The damaged or dead cells may then be resorbed by the body over time, reducing the amount of fat present in the treated area.

The cutting arrangement 810 can include, for example, one or more thin wires, blades, or the like that extend across a portion of the lumen of the needle 120. End views of two exemplary cutting arrangements 810 are shown in FIGS. 8B and 8C. The cutting arrangement 810 in FIGS. 8B and 8C can include a plurality of thin wires or blades attached to the inner wall of the needle 120, and traversing a portion of the lumen. Other configurations of the cutting arrangement 810 can be provided in further embodiments of the disclosure.

The exemplary apparatus 800 can be inserted into skin tissue and then withdrawn as described herein, for example, with respect to other exemplary embodiments of the present disclosure. Such exemplary insertion and withdrawal of the exemplary apparatus 800 can cause a portion of the fat layer 210 to enter the lumen of the needle 120, with the overlying dermis layer 220 remaining substantially unaffected after the apparatus 800 is fully withdrawn. The fat tissue that enters the lumen may be damaged by the cutting arrangement 810 during the insertion and withdrawal procedures. The exemplary apparatus can may be partially withdrawn from the skin and then advanced again a plurality of times before fully withdrawing it from the skin. For example, the exemplary apparatus 800 can be withdrawn until the distal end 110 is proximal to the lower portion of the dermal layer 220, and then re-advanced deeper into the fat layer 210. Such repeated cycles can create a greater degree of local damage to the fat tissue. Little or no fat may remain within the lumen when the apparatus 800 is withdrawn from the skin. However, the damaged fat cells may die and be resorbed by the body over time.

The features of the exemplary apparatus 800 can be used in conjunction with the other exemplary embodiments described herein. For example, a plurality of needles 120 that include a cutting arrangement 810 can be affixed to a substrate 330, e.g., as shown in FIGS. 3A-3C. One or more such needles 120 can also be coupled to a reciprocating arrangement 420 as illustrated in FIG. 4, to generate damage in a broader region of the fat layer 210.

The exemplary apparatus 800 can include a plurality of needles 120 having different types of fat-disrupting arrangements as described herein. For example, different ones of the needles 120 may include a protrusion 130, a pivoting flap 510, or a cutting arrangement 810. In another exemplary embodiment, a plurality of needles 120 containing different types of such fat disruption arrangements 130, 510, 810 can be mechanically coupled to a reciprocating arrangement 420 as described herein. Different ones of the needles 120 in such multi-needle devices can optionally have different lengths, which can facilitate harvesting or damaging of fat at different depths within the fat layer 210.

In further exemplary embodiments of the present disclosure, a vibrating arrangement can be mechanically coupled to any exemplary apparatus described herein. Inducing vibration in the needles 120 can facilitate detachment of fat portions 230 from the surrounding tissue and/or can generate a greater mechanical damage by a cutting arrangement provided in the needle 120.

The exemplary methods and devices described herein can be used for a variety of purposes, for example, to remove small portions of the fatty tissue for cosmetic purposes, to harvest stem cells that may be present in regions of the subcutaneous fat layer to harvest fatty tissue for implantation in other portions of the body for cosmetic purposes, and/or to generate mechanical damage of fat cells to promote cell death and resorption of damaged fat by the body.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein embody the principles of the present disclosure and are thus within the spirit and scope of the present disclosure. All patents and publications cited herein are incorporated herein by reference in their entireties.

What is claimed is:

1. A method for removing subcutaneous fatty tissue from skin tissue, comprising:
    inserting a plurality of hollow needle arrangements into the skin tissue, wherein the hollow needle arrangements are mechanically coupled to a substrate, each hollow needle arrangement having a central lumen, a proximal end, and a distal end, and wherein the hollow needle arrangements are inserted into the skin tissue until at least the distal portion of each hollow needle arrangement is located within the subcutaneous fatty tissue below dermal tissue of the skin tissue; and
    withdrawing the plurality of hollow needle arrangements from the skin tissue, wherein: the distal end of each of the plurality of hollow needle arrangements is configured to distinguish the subcutaneous fatty tissue from the dermal tissue to substantially prevent the dermal tissue from entering the central lumen of any of the hollow needle arrangements and to allow a portion of the subcutaneous fatty tissue to enter the central lumen of each of the hollow needle arrangements; and
    the plurality of hollow needle arrangements are each in communication with a common vacuum or suction source to remove the subcutaneous fatty tissue that has entered the central lumens.

2. The method of claim 1, wherein the plurality of hollow needle arrangements is in communication with the common vacuum or suction source via a conduit in communication with the proximal end of each of the hollow needle arrangements.

3. The method of claim 1, comprising applying a pressure less than atmospheric or ambient pressure in the central lumen of each of the hollow needle arrangements to facilitate removal of a portion of fatty tissue when the distal end of each of the hollow needle arrangements is located within the subcutaneous fatty tissue.

4. The method of claim 1, further comprising:
removing a sample of the portion of the fatty tissue from the skin tissue when the plurality of hollow needle arrangements is withdrawn from the skin tissue.

5. The method of claim 1, further comprising:
generating mechanical damage to the portion of the fatty tissue when the plurality of hollow needle arrangements is inserted into the skin tissue.

6. The method of claim 1, wherein the distal end of each of the hollow needle arrangements is configured to be inserted into skin tissue, pass through a dermal layer thereof, and prevent a significant portion of the dermal tissue from entering the central lumen.

7. The method of claim 1, wherein the distal end of each of the hollow needle arrangements is provided as an angled tip, and wherein an angle of the tip is between about 30 degrees and about 50 degrees.

8. The method of claim 1, wherein a diameter of the central lumen of each of the hollow needle arrangements is about 1.25 mm.

9. The method of claim 1, comprising repeatedly inserting and withdrawing the plurality of hollow needle arrangements from the skin tissue.

10. The method of claim 9, wherein the repeated inserting and withdrawing the plurality of hollow needle arrangements is carried out using a reciprocating arrangement comprising an actuator and a control arrangement.

11. The method of claim 1, comprising translating the plurality of hollow needle arrangements over the skin tissue in one or two orthogonal directions.

12. The method of claim 11, wherein translating the plurality of hollow needle arrangements is carried out using a reciprocating arrangement comprising an actuator and a control arrangement.

13. The method of claim 1, comprising vibrating, by a vibrating source, the plurality of hollow needle arrangements to facilitate detachment of the portion of the subcutaneous fatty tissue from surrounding tissue.

14. The method of claim 1, comprising partially withdrawing the plurality of hollow needle arrangements from the skin tissue and then advancing the plurality of hollow needle arrangements again a plurality of times before fully withdrawing it from the skin tissue.

15. The method of claim 1, comprising stretching the skin tissue when the plurality of hollow needle arrangements is placed on the skin tissue to be treated.

16. The method of claim 1, wherein each of the hollow needle arrangements comprises at least one protrusion provided along at least one portion of an interior wall of the hollow needle arrangement, wherein the at least one protrusion is configured to remove the portion of the subcutaneous fatty tissue.

17. The method of claim 1, wherein each of the hollow needle arrangements comprises at least one cutting arrangement provided in distal portion of the central lumen.

18. The method of claim 1, comprising adjusting a protrusion distance of the plurality of the hollow needle arrangements from an apparatus comprising the substrate.

\* \* \* \* \*

UNITED STATES PATENT AND TRADEMARK OFFICE
CERTIFICATE OF CORRECTION

PATENT NO. : 11,337,720 B2
APPLICATION NO. : 15/916020
DATED : May 24, 2022
INVENTOR(S) : William G. Austen Page 1 of 1

It is certified that error appears in the above-identified patent and that said Letters Patent is hereby corrected as shown below:

In the Specification

Column 6, Line 16, "hack" should be --back--.

Signed and Sealed this
Twenty-sixth Day of July, 2022

Katherine Kelly Vidal
*Director of the United States Patent and Trademark Office*